United States Patent [19]
Munden

[11] Patent Number: 5,853,732
[45] Date of Patent: Dec. 29, 1998

[54] PHARMACEUTICAL COMPOSITIONS CONTAINING KUKUI NUT OIL

[75] Inventor: James W. Munden, Portage, Mich.

[73] Assignee: Pharmacia & Upjohn Company, Kalamazoo, Mich.

[21] Appl. No.: 958,273

[22] Filed: Oct. 27, 1997

Related U.S. Application Data

[60] Provisional application No. 60/032,048 Nov. 12, 1996.

[51] Int. Cl.[6] .......................... A61K 35/78; A61K 47/44; A61K 9/06
[52] U.S. Cl. ..................... 424/195.1; 514/783; 514/786; 514/844; 514/969
[58] Field of Search ........................................... 424/195.1

[56] References Cited

U.S. PATENT DOCUMENTS

| | | | |
|---|---|---|---|
| 4,154,823 | 5/1979 | Schutt | ..................... 424/195 |
| 4,525,344 | 6/1985 | Tutsky . | |
| 5,213,798 | 5/1993 | Manikas et al. . | |
| 5,279,817 | 1/1994 | Franco | ..................... 424/59 |
| 5,560,917 | 10/1996 | Cohen et al. . | |
| 5,626,155 | 5/1997 | Saute et al. . | |
| 5,656,312 | 8/1997 | Collett et al. . | |
| 5,720,942 | 2/1998 | Johnson . | |

FOREIGN PATENT DOCUMENTS

| | | | |
|---|---|---|---|
| 44 05 127A | 8/1995 | Germany | ......................... A61K 7/06 |
| 85 00746A | 2/1985 | WIPO | ............................. A61K 7/15 |

OTHER PUBLICATIONS

Gray Drug & Cosmetic Industry 150(5) 38, 92–94, All Vegetable Oils Aren't Created Equal, 1992.

Anon SPC (Soap Perfumery & Cosmetics 64(11) 49, 51–52 Waxing Lyrical on Oil, Nov. 1991.

*Hawaii Dental Journal*, pp. 8 and 13 (1986).

H. Ako et al., *J. Soc. Cosmet. Chem.*, vol. 44, pp. 239–247 (1993).

I. A. Abbott and C. Shimazu, *J. Ethnopharm.*, vol. 14, pp. 213–222, (1985).

J. Brod et al., *International Journal of Cosmetic Science*, vol. 10, pp. 149–159 (1988).

K. Klein, *Cosmetics & Toiletries*, vol. 106, pp. 87–88 (1991).

JP7025741 A (abstract)—Database WPI, Week 9514, Derwent Publications ltd., London GB: AN 95–101776, XP002052527.

*Primary Examiner*—Shep K. Rose
*Attorney, Agent, or Firm*—Lucy X. Yang

[57] ABSTRACT

The present invention provides pharmaceutical compositions comprising an effective amount of dermopharmaceutical active agent, kukui nut oil and a pharmaceutically acceptable base which comprises ingredients selected from the group consisting of propylene glycol, glycerin, xanthin gum, methyl paraben, propyl paraben, stearic acid, menthyl lactate, cetearyl alcohol (and) ceteareth 20, polyoxyl 40 stearate, glyceryl stearate (and) PEG-100 stearate, isopropyl myristate, isopropyl alcohol, oleyl alcohol, oleic acid, dimethicone, or $C_{12}$–$C_{15}$ alcohols benzoate and purified water.

The inclusion of kukui nut oil acts in synergy as an adjunct to the therapeutic agent to promote the alleviation of the medical condition being treated.

13 Claims, No Drawings

PHARMACEUTICAL COMPOSITIONS CONTAINING KUKUI NUT OIL

CROSS-REFERENCE TO RELATED APPLICATION

This application claims the benefit of the following provisional application: U.S. Ser. No. 60/032,048 filed Nov. 12, 1996, under 35 USC 119(e)(i).

FIELD OF THE INVENTION

The present invention relates to pharmaceutical compositions which are useful for the treatment of human skin disorder. The compositions comprise, a pharmaceutically acceptable base, an active dermopharmaceutical agent and kukui nut oil.

BACKGROUND OF THE INVENTION

Topical application of drugs to the skin surface has been used since antiquity to treat diseases of the skin. Skin has the tendency to dry out when exposed to conditions of low humidity or to an extended period of time in chemicals. A common finding in patients with skin diseases is the high incidence of dry skin, i.e. the inflamed skin surface feels rough to the touch. See: "Bioengineering of the Skin: Water and the Stratum Corneum", Chapter 8. CRC Press, Inc., London, pp. 87–132 (1994). Although the treatment of human skin with various agents has been undertaken for many years in the cosmetic field with the goal to keep the skin in a smooth supple condition, the consideration has never been taken to mind when dermopharmaceutical compositions are proposed.

On the other hand, it is known that mineral hydrocarbons (petrolatum derivatives) are extensively used in pharmaceutical and cosmetic compositions as well as in various food products. Recently, there are safety concerns over the use of these mineral hydrocarbons in pharmaceutical, cosmetic, and food products.

Accordingly, the object of the present invention is to provide therapeutically active compositions for the treatment of human skin diseases.

More particularly, the object of the present invention is to provide therapeutic compositions which have additional skin care benefits to the patients whose skin disorders are accompanied by dryness which demand treatments beyond solely using topically applied drugs.

Another object of the present invention is to provide a pharmaceutically acceptable base containing natural oils as an alternative to mineral oil in formulating therapeutically active compositions.

After various searches on a large number of substances, it has been discovered that incorporation of kukui nut oil into certain stable cream, lotion, or ointment bases which contain an effective amount of active dermopharmaceutical agent, such as a corticosteroid, antibiotic, antihistamine, antifungal, anesthetic, or analgesic, have a particularly pronounced synergic effect.

Experiments have also been conducted to determine if various natural oils could be substituted for mineral oil one to one in typical oil and water emulsion in the pharmaceutical and cosmetic compositions. Based on the studies, however, it is determined that kukui nut oil is one of several vegetable oils which are non-viable alternatives to mineral oil in formulating typical cosmetic and pharmaceutical creams or lotions. Surprisingly and unexpectedly, the compositions of the present invention provide pharmaceutically acceptable bases containing kukui nut oil which can be used as active dermopharmaceutical agent carriers.

INFORMATION DISCLOSURE

Kukui nut tree, is a native tree in all countries from western Polynesia to southern Asia and is generally found in woods of lower mountain zone, web gushes and valleys, ravines and hanging valleys of tropics and subtropics. In the United States, the kukui tree is found in all islands of Hawaii. Certain medicinal and other uses of various portions of the kukui nut tree or its nut have been reported, particularly in native Hawaiian medicine, the kukui nut has many uses.

*Hawaii Dental Journal*, pages 8 and 13 (1986), discloses several uses of kukui nut tree. Kukui flowers, baked kukui nut and sugarcane mixture are used for stomachache and bowel disorders. Kukui bark is used in herbal tea. Chronic ulcers and scrofula are treated with mixture containing kukui meat and kukui nut cooled in kukui leaves. Sap from the kukui nut tree is used to treat bad breath and coated tongue. The juice of the kukui fruit are used as a mouthwash, for the treatment of a fungal infection thrush or moniliasis, and for other superficial internal oral lesions.

U.S. Pat. No. 5,213,798 discloses the use of the active ingredient present in the liquid obtained from the green hull of the kukui nut as an antiviral pharmaceutical agent.

U.S. Pat. No. 4,525,344 discloses a combination skin care and shaving composition containing kukui nut oil.

U.S. Pat. No. 4,525,344 discloses suntanning oil formulation containing kukui nut oil.

Additional references of general interest include the following:

H. Ako et al., *J. Soc. Cosmet. Chem.*, Vol. 44, pp. 239–247 (1993); I. A. Abbott and C. Shimazu, *J. Ethnopharm.*, Vol. 14, pp. 213–222, (1985); J. Brod et al., *International journal of Cosmetic Science*, Vol. 10, pp. 149–159 (1988); and K. Klein, *Cosmetics & Toiletries*, Vol. 106, pp. 87–88 (1991).

While certain properties of the kukui nut are known, there has been no reports or suggestions regarding the use of kukui nut oil in combination with active pharmaceutical agents for the treatment of the skin diseases.

SUMMARY OF THE INVENTION

This invention provides a pharmaceutical composition comprising: a) an effective amount of dermopharmaceutical active agent, b) about 1.0% to about 10% of kukui nut oil by weight of the total composition, and c) up to about 98% by weight of the total composition of a pharmaceutically acceptable base which comprises ingredients selected from the group consisting of propylene glycol, glycerin, xanthin gum, methyl paraben, propyl paraben, stearic acid, menthyl lactate, cetearyl alcohol (and) ceteareth 20, polyoxyl 40 stearate, glyceryl stearate (and) PEG-100 stearate, isopropyl myristate, isopropyl alcohol, oleyl alcohol, oleic acid, dimethicone, or $C_{12}$–$C_{15}$ alcohols benzoate and purified water.

The inclusion of kukui nut oil acts in synergy as an adjunct to the therapeutic agent to promote the alleviation of the medical condition being treated.

DETAILED DESCRIPTION OF THE INVENTION

Kukui nut oil, extracted from the nuts of kukui nut trees, has been used for hundreds of years by native Hawaiians to treat a variety of ailments. Of particular note is the application to skin disorders. The rapid penetration of the oil into the skin has been shown to bring rapid, soothing relief for superficial burns, chapped skin, and minor skin diseases. Application prior to exposure of the skin to challenges such as wind and sun also help prevent skin damage from occurring. The inclusion of kukui nut oil acts in synergy as an adjunct to the therapeutic agent to promote the alleviation of the medical condition being treated. The results of these combinations against inflamed, infected, or other skin disorders are more effective than each of the components, the kukui nut oil, on the one hand, or active dermopharmaceutical agents, on the other hand, when the latter are taken separately, at comparable concentrations.

The pharmaceutical compositions of this invention may be prepared by combining an active dermopharmaceutical agent with kukui nut oil, in a pharmaceutically acceptable base.

The term "kukui nut oil" refers to the fat obtained from the nut of a kukui tree, also known as *Aleurites moluccana* or the candlenut tree. An example of such oil is the natural kukui nut oil, sold under the trade name "Oils of Aloha™" by the Hawaiian Kukui Nut Company.

The kukui nut oil is present in the compositions of this invention at a concentration of from about 0.5% to about 10%, preferably at a concentration of about 2%.

The term "active dermopharmaceutical agents" refers to corticosteroid, analgesics, anesthetics, antibiotics, antihistamines, and antifungals, particularly referring to corticosteroids such as hydrocortisone.

The active dermopharmaceutical agents are present in the compositions at a normal range commonly known and well accepted by physicians of ordinary skill and those skilled in the pharmaceutical field. For example, the normal range of hydrocortisone in topical products is at a concentration of from 0.5% to 2.5% by weight; the normal range of anesthetic such as lidocaine in topical products is at a concentration of from 0.5% to 4% by weight, higher concentrations are present in some prescription (Rx) products; the normal range of antihistamine or diphenhydramine in topical products is at a concentration of from 0.5% to 2.5% by weight; the normal range of zinc oxide in topical products is at a concentration of from 1% to 25% by weight; and the normal range of urea in topical products is at a concentration of from 5% to 10% by weight.

The term "pharmaceutically acceptable base" refers to ingredients which are acceptable in the pharmaceutical sciences as a drug carrier. For the present invention, the pharmaceutically acceptable base comprises ingredients selected from the group consisting of propylene glycol, glycerin, xanthin gum, methyl paraben, propyl paraben, stearic acid, menthyl lactate, cetearyl alcohol (and) ceteareth 20, polyoxyl 40 stearate, glyceryl stearate (and) PEG-100 stearate, isopropyl myristate, isopropyl alcohol, oleyl alcohol, oleic acid, dimethicone or $C_{12}$–$C_{15}$ alcohols benzoate, and purified water. All these ingredients are commercially available and do not require any special preparation before use.

The pharmaceutical compositions of this invention can optionally contain conventional coloring agents, fragrances, stabilizers and thickening agents.

The pharmaceutical compositions of this invention are provided in a form intended to be applied topically such as, for example, lotion, thickened lotion, gel cream, milk, ointment, or vesicular dispersion, preferably in the forms of lotion and cream.

The term "skin disorders" or "skin diseases" means the diseases associated with inflammation, infections such as fungal and bacterial infections, dermatitis, psoriasis, eczema, and allergies. Such diseases and conditions are well known and readily diagnosed by physicians of ordinary skill.

The term "Promulgen D" refers to a mixture of cetearyl alcohol and ceteareth 20 known under CTFA terminology as "cetearyl alcohol (and) ceteareth 20". Promulgen D is sold under the trademark PROMULGEN®D.

The term "Arlacel 165" refers to a mixture of glyceryl stearate and PEG-100 stearate known under the CTFA nomenclature as "glyceryl stearate (and) PEG-100 stearate". Arlacel 165 is sold under the trademark ARLACEL® 165.

The term "Finsolv TN" refers to a mixture of $C_{12}$–$C_{15}$ alcohols benzoate known under CTFA nomenclature as "$C_{12}$–$C_{15}$ alcohols benzoate". Finsolv TN is sold under the trademark FINSOLV TN.

CTFA refers to the Cosmetic, Toiletries, and Fragrances Association.

The term "q.s." refers to quantum sufficit or as much as being sufficient.

The term "q.s. ad" refers to addition of a sufficient quantity of that material to bring the final composition to the specified volume.

All temperatures are in degrees Centigrade.

The pharmaceutical compositions of this invention are seen more fully by the examples given below.

LOTION BASE EXAMPLE #1

| Ingredients | Approximate Percent (w/w) |
| --- | --- |
| Glycerin NF | 2.0% |
| Xanthan gum NF | 0.2% |
| Methyl paraben NF | 0.2% |
| Propyl paraben NF | 0.1% |
| Promulgen D | 3.0% |
| Arlacel 165 | 10.0% |
| Isopropyl Myristate | 5.0% |
| Oleyl Alcohol | 5.0% |
| Finsolv TN | 6.0% |
| Kukui Nut Oil | 2.0% |
| Dimethicone | 2.0% |
| Purified Water | q.s. ad 100.0% |

Heat a portion of the water to 65° C. Disperse the xanthan gum in the glycerin and add to the water with agitation. Melt the Promulgen, Arlacel, isopropyl myristate, oleyl alcohol, Finsolv TN, and kukui nut oil together at 65° C. Dissolve the parabens in the oils. Then add the oil phase to the water phase with rapid mixing. Remove heat and add the volatile silicone. Rapidly cool to 40° C. once the emulsion is formed. Continue mixing until room temperature is reached. Perform final q.s.

LOTION BASE EXAMPLE #2

| Ingredients | Approximate Percent (w/w) |
| --- | --- |
| Propylene Glycol | 2.0% |
| Xanthan gum NF | 0.2% |
| Methyl paraben NF | 0.2% |
| Propyl paraben NF | 0.1% |
| Promulgen D | 3.0% |
| Arlacel 165 | 10.0% |
| Isopropyl Myristate | 5.0% |

-continued

LOTION BASE EXAMPLE #2

| Ingredients | Approximate Percent (w/w) |
| --- | --- |
| Oleyl Alcohol | 5.0% |
| Finsolv TN | 6.0% |
| Kukui Nut Oil | 2.0% |
| Dimethicone | 2.0% |
| Purified Water | q.s. ad 100.0% |

Heat a portion of the water to 65° C. Disperse the xanthan gum in the propylene glycol and add to the water with agitation. Melt the Promulgen, Arlacel, isopropyl myristate, oleyl alcohol, Finsolv TN, and kukui nut oil together at 65° C. Dissolve the parabens in the oils. Then add the oil phase to the water phase with rapid mixing. Remove heat and add the volatile silicone. Rapidly cool to 40° C. once the emulsion is formed. Continue mixing until room temperature is reached. Perform final q.s.

LOTION BASE EXAMPLE #3

| Ingredients | Approximate Percent (w/w) |
| --- | --- |
| Propylene Glycol | 2.0% |
| Xanthan gum NF | 0.2% |
| Methyl paraben NF | 0.2% |
| Propyl paraben NF | 0.1% |
| Promulgen D | 3.0% |
| Arlacel 165 | 10.0% |
| Isopropyl Myristate | 5.0% |
| Oleic Acid | 5.0% |
| Finsolv TN | 6.0% |
| Kukui Nut Oil | 2.0% |
| Dimethicone | 2.0% |
| Purified Water | q.s. ad 100.0% |

Heat a portion of the water to 65° C. Disperse the xanthan gum in the propylene glycol and add to the water with agitation. Melt the Promulgen, Arlacel, isopropyl myristate, oleic acid, Finsolv TN, and kukui nut oil together at 65° C. Dissolve the parabens in the oils. Then add the oil phase to the water phase with rapid mixing. Remove heat and add the volatile silicone. Rapidly cool to 40° C. once the emulsion is formed. Continue mixing until room temperature is reached. Perform final q.s.

CREAM BASE EXAMPLE #4

| Ingredients | Approximate Percent (w/w) |
| --- | --- |
| Glycerin NF | 2.0% |
| Methyl paraben NF | 0.2% |
| Propyl paraben NF | 0.1% |
| Stearic Acid NF | 8.0% |
| Polyoxyl 40 Stearate NF | 4.0% |
| Arlacel 165 | 10.0% |
| Isopropyl Myristate | 5.0% |
| Oleyl Alcohol | 5.0% |
| Kukui Nut Oil | 2.0% |
| Dimethicone | 2.0% |
| Purified Water | q.s. ad 100.0% |

Heat a portion of the water to 65° C. Disperse the methyl paraben in the glycerin and add to the water with agitation. Melt the stearic acid, Arlacel, polyoxyl 40 stearate, isopropyl myristate, oleyl alcohol, and kukui nut oil together at 65° C. Dissolve the propyl paraben in the oils. Then add the oil phase to the water phase with rapid mixing. Remove heat and add the volatile silicone. Rapidly cool to 40° C. once the emulsion is formed. Continue mixing until room temperature is reached. Perform final q.s.

CREAM BASE EXAMPLE #5

| Ingredients | Approximate Percent (w/w) |
| --- | --- |
| Glycerin NF | 2.0% |
| Methyl paraben NF | 0.2% |
| Propyl paraben NF | 0.1% |
| Stearic Acid NF | 8.0% |
| Polyoxyl 40 Stearate NF | 4.0% |
| Arlacel 165 | 10.0% |
| Isopropyl Myristate | 5.0% |
| Oleic Acid | 5.0% |
| Kukui Nut Oil | 2.0% |
| Dimethicone | 2.0% |
| Purified Water | q.s. ad 100.0% |

Heat a portion of the water to 65° C. Disperse the methyl paraben in the glycerin and add to the water with agitation. Melt the stearic acid, Arlacel, polyoxyl 40 stearate, isopropyl myristate, oleic acid, and kukui nut oil together at 65° C. Dissolve the propyl paraben in the oils. Then add the oil phase to the water phase with rapid mixing. Remove heat and add the volatile silicone. Rapidly cool to 40° C. once the emulsion is formed. Continue mixing until room temperature is reached. Perform final q.s.

CREAM BASE EXAMPLE #6

| Ingredients | Approximate Percent (w/w) |
| --- | --- |
| Propylene Glycol | 2.0% |
| Methyl paraben NF | 0.2% |
| Propyl paraben NF | 0.1% |
| Stearic Acid NF | 8.0% |
| Polyoxyl 40 Stearate NF | 4.0% |
| Arlacel 165 | 10.0% |
| Isopropyl Myristate | 5.0% |
| Oleyl Alcohol | 5.0% |
| Kukui Nut Oil | 2.0% |
| Dimethicone | 2.0% |
| Purified Water | q.s. ad 100.0% |

Heat a portion of the water to 65° C. Disperse the methyl paraben in the propylene glycol and add to the water with agitation. Melt the stearic acid, Arlacel, polyoxyl 40 stearate, isopropyl myristate, oleyl alcohol, and kukui nut oil together at 65° C. Dissolve the propyl paraben in the oils. Then add the oil phase to the water phase with rapid mixing. Remove heat and add the volatile silicone. Rapidly cool to 40° C. once the emulsion is formed. Continue mixing until room temperature is reached. Perform final q.s.

LOTION BASE EXAMPLE #7

| Ingredients | Approximate Percent (w/w) |
| --- | --- |
| Propylene Glycol | 2.0% |
| Methyl paraben NF | 0.2% |
| Propyl paraben NF | 0.1% |
| Polyoxyl 40 Stearate NF | 4.0% |
| Arlacel 165 | 10.0% |
| Isopropyl Myristate | 5.0% |
| Isostearyl Alcohol | 5.0% |
| Kukui Nut Oil | 2.0% |
| Dimethicone | 2.0% |
| Fragrance | q.s. |
| Purified Water | q.s. ad 100.0% |

Heat a portion of the water to 65° C. Disperse the methyl paraben in the propylene glycol and add to the water with agitation. Melt the Arlacel, polyoxyl 40 stearate, isopropyl myristate, isostearyl alcohol, and kukui nut oil together at 65° C. Dissolve the propyl paraben in the oils. Then add the oil phase to the water phase with rapid mixing. Remove heat and add the volatile silicone. Rapidly cool to 40° C. once the emulsion is formed. Add fragrance. Continue mixing until room temperature is reached. Perform final q.s.

CREAM BASE EXAMPLE #8

| Ingredients | Approximate Percent (w/w) |
|---|---|
| Propylene Glycol | 2.0% |
| Methyl paraben NF | 0.2% |
| Propyl paraben NF | 0.1% |
| Stearic Acid NF | 8.0% |
| Polyoxyl 40 Stearate NF | 4.0% |
| Arlacel 165 | 10.0% |
| Isopropyl Myristate | 5.0% |
| Isostearyl Alcohol | 5.0% |
| Kukui Nut Oil | 2.0% |
| Dimethicone | 2.0% |
| Purified Water | q.s. ad 100.0% |

Heat a portion of the water to 65° C. Disperse the methyl paraben in the propylene glycol and add to the water with agitation. Melt the stearic acid, Arlacel, polyoxyl 40 stearate, isopropyl myristate, oleyl alcohol, and kukui nut oil together at 65° C. Dissolve the propyl paraben in the oils. Then add the oil phase to the water phase with rapid mixing. Remove heat and add the volatile silicone. Rapidly cool to 40° C. once the emulsion is formed. Continue mixing until room temperature is reached. Perform final q.s.

CREAM BASE EXAMPLE #9

| Ingredients | Approximate Percent (w/w) |
|---|---|
| Propylene Glycol | 2.0% |
| Methyl paraben NF | 0.2% |
| Propyl paraben NF | 0.1% |
| Stearic Acid NF | 8.0% |
| Polyoxyl 40 Stearate NF | 4.0% |
| Arlacel 165 | 10.0% |
| Isopropyl Myristate | 5.0% |
| Isostearyl Alcohol | 5.0% |
| Kukui Nut Oil with Fragrance | 2.0% |
| Dimethicone | 2.0% |
| Purified Water | q.s. ad 100.0% |

Heat a portion of the water to 65° C. Disperse the methyl paraben in the propylene glycol and add to the water with agitation. Melt the stearic acid, Arlacel, polyoxyl 40 stearate, isopropyl myristate, isostearyl alcohol, and kukui nut oil together at 65° C. Dissolved the propyl paraben in the oils. Then add the oil phase to the water phase with rapid mixing. Remove heat and add the volatile silicone. Rapidly cool to 40° C. once the emulsion is formed. Continue mixing until room temperature is reached. Perform final q.s.

CREAM BASE EXAMPLE #10

| Ingredients | Approximate Percent (w/w) |
|---|---|
| Propylene Glycol | 2.0% |
| Methyl paraben NF | 0.2% |
| Propyl paraben NF | 0.1% |
| Stearic Acid NF | 8.0% |
| Polyoxyl 40 Stearate NF | 4.0% |
| Arlacel 165 | 10.0% |
| Isopropyl Myristate | 5.0% |
| Isostearyl Alcohol | 5.0% |
| Kukui Nut Oil | 2.0% |
| Dimethicone | 2.0% |
| Petals Fragrance G7042 | 0.3% |
| Purified Water | q.s. ad 100.0% |

Heat a portion of the water to 65° C. Disperse the methyl paraben in the propylene glycol and add to the water with agitation. Melt the stearic acid, Arlacel, polyoxyl 40 stearate, isopropyl myristate, isostearyl alcohol, and kukui nut oil together at 65° C. Dissolve the propyl paraben in the oils. Then add the oil phase to the water phase with rapid mixing. Remove heat and add the volatile silicone and the fragrance. Perform the final q.s. Rapidly cool to 40° C. once the emulsion is formed. Continue mixing until room temperature is reached.

CREAM BASE EXAMPLE BASE #11

| Ingredients | Approximate Percent (w/w) |
|---|---|
| Propylene Glycol | 2.0% |
| Methyl paraben NF | 0.2% |
| Propyl paraben NF | 0.1% |
| Promulgen D | 8.0% |
| Polyoxyl 40 Stearate NF | 4.0% |
| Arlacel 165 | 10.0% |
| Isopropyl Myristate | 5.0% |
| Isostearyl Alcohol | 5.0% |
| Kukui Nut Oil | 2.0% |
| Fragrance (optional) | q.s. |
| Purified Water | q.s. ad 100.0% |

Heat a portion of the water to 65° C. Disperse the methyl paraben in the propylene glycol and add to the water with agitation. Melt the Promulgen D, Arlacel, polyoxyl 40 stearate, isopropyl myristate, isostearyl alcohol, and kukui nut oil together at 65° C. Dissolve the propyl paraben in the oils. Then add the oil phase to the water phase with rapid mixing. Remove heat and add the fragrance. Perform the final q.s. Rapidly cool to 40° C. once the emulsion is formed. Continue mixing until room temperature is reached.

LOTION BASE EXAMPLE #12

| Ingredients | Approximate Percent (w/w) |
|---|---|
| Propylene Glycol | 2.0% |
| Methyl paraben NF | 0.2% |
| Propyl paraben NF | 0.1% |
| Promulgen D | 2.0% |
| Polyoxyl 40 Stearate NF | 4.0% |
| Arlacel 165 | 10.0% |
| Isopropyl Myristate | 5.0% |
| Isostearyl Alcohol | 5.0% |
| Kukui Nut Oil | 2.0% |
| Dimeticone | 2.0% |
| Fragrance (optional) | q.s. |
| Purified Water | q.s. ad 100.0% |

Heat a portion of the water to 65° C. Disperse the methyl paraben in the propylene glycol and add to the water with agitation. Melt the Promulgen D, Arlacel, polyoxyl 40 stearate, isopropyl myristate, isostearyl alcohol, and kukui nut oil together at 65° C. Dissolve the propyl paraben in the oils. Then add the oil phase to the water phase with rapid mixing. Remove heat and add the fragrance and the volatile silicone. Perform the final q.s. Rapidly cool to 40° C. once the emulsion is formed. Continue mixing until room temperature is reached.

LOTION BASE EXAMPLE #13

| Ingredients | Approximate Percent (w/w) |
| --- | --- |
| Propylene Glycol | 2.0% |
| Methyl paraben NF | 0.2% |
| Propyl paraben NF | 0.1% |
| Promulgen D | 4.0% |
| Polyoxyl 40 Stearate NF | 4.0% |
| Arlacel 165 | 10.0% |
| Isopropyl Myristate | 5.0% |
| Isostearyl Alcohol | 5.0% |
| Kukui Nut Oil | 2.0% |
| Dimeticone | 2.0% |
| Fragrance (optional) | q.s. |
| Purified Water | q.s. ad 100.0% |

Heat a portion of the water to 65° C. Disperse the methyl paraben in the propylene glycol and add to the water with agitation. Melt the Promulgen D, Arlacel, polyoxyl 40 stearate, isopropyl myristate, isostearyl alcohol, and kukui nut oil together at 65° C. Dissolve the propyl paraben in the oils. Then add the oil phase to the water phase with rapid mixing. Remove heat and add the fragrance and volatile silicone. Perform the final q.s. Rapidly cool to 40° C. once the emulsion is formed. Continue mixing until room temperature is reached.

CREAM BASE WITH HYDROCORTISONE EXAMPLE #14

| Ingredients | Approximate Percent (w/w) |
| --- | --- |
| Propylene Glycol | 2.0% |
| Hydrocortisone | 1.0% |
| Methyl paraben NF | 0.2% |
| Propyl paraben NF | 0.1% |
| Promulgen D | 8.0% |
| Polyoxyl 40 Stearate NF | 4.0% |
| Arlacel 165 | 10.0% |
| Isopropyl Myristate | 5.0% |
| Isostearyl Alcohol | 5.0% |
| Kukui Nut Oil | 2.0% |
| Dimethicone | 1.0% |
| Fragrance (optional) | q.s. |
| Purified Water | q.s. ad 100.0% |

Heat a portion of the water to 65°–70° C. Disperse the methyl paraben in the propylene glycol and add to the water with agitation. Add the polyoxyl 40 stearate and dissolve. Add the hydrocortisone and disperse using a high shear mixer or similar. Melt the Promulgen D, Arlacel, isopropyl myristate, isostearyl alcohol, and kukui nut oil together at 65°–70° C. Dissolve the propyl paraben in the oils. Then add the oil phase to the water phase with rapid mixing. Remove heat and add the dimethicone and fragrance. Perform the final q.s. Rapidly cool to 40° C. once the emulsion is formed. Continue mixing until room temperature is reached.

LOTION BASE WITH LIDOCAINE HYDROCHLORIDE EXAMPLE #15

| Ingredients | Approximate Percent (w/w) |
| --- | --- |
| Propylene Glycol | 2.0% |
| Lidocaine Hydrochloride | 4.0% |
| Methyl paraben NF | 0.2% |
| Propyl paraben NF | 0.1% |
| Promulgen D | 6.0% |
| Polyoxyl 40 Stearate NF | 4.0% |
| Arlacel 165 | 10.0% |
| Isopropyl Myristate | 5.0% |
| Isostearyl Alcohol | 5.0% |
| Kukui Nut Oil | 2.0% |
| Dimethicone | 1.0–2.0% |
| Fragrance (optional) | q.s. |
| Purified Water | q.s. ad 100.0% |

Heat a portion of the water to 65°–70° C. Disperse the methyl paraben in the propylene glycol and add to the water with agitation. Add the lidocaine and dissolve. Melt the polyoxyl 40 stearate, Promulgen D, Arlacel, isopropyl myristate, isostearyl alcohol, and kukui nut oil together at 65°–70° C. Dissolve the propyl paraben in the oils. Then add the oil phase to the water phase with rapid mixing. Remove heat and add the dimethicone and fragrance. Perform the final q.s. Rapidly cool to 40° C. once the emulsion is formed. Continue mixing until room temperature is reached.

LOTION BASE WITH LIDOCAINE HYDROCHLORIDE EXAMPLE #16

| Ingredients | Approximate Percent (w/w) |
| --- | --- |
| Propylene Glycol | 2.0% |
| Lidocaine Hydrochloride | 4.0% |
| Methyl paraben NF | 0.2% |
| Propyl paraben NF | 0.1% |
| Promulgen D | 4.0% |
| Polyoxyl 40 Stearate NF | 2.0% |
| Arlacel 165 | 10.0% |
| Isopropyl Myristate | 5.0% |
| Isostearyl Alcohol | 5.0% |
| Kukui Nut Oil | 2.0% |
| Dimethicone | 1.0% |
| Fragrance (optional) | q.s. |
| Purified Water | q.s. ad 100.0% |

Heat a portion of the water to 65°–70° C. Disperse the methyl paraben in the propylene glycol and add to the water with agitation. Add the lidocaine and dissolve. Melt the polyoxyl 40 stearate, Promulgen D, Arlacel, , isopropyl myristate, isostearyl alcohol, and kukui nut oil together at 65°–70° C. Dissolve the propyl paraben in the oils. Then add the oil phase to the water phase with rapid mixing. Remove heat and add the dimethicone and fragrance. Perform the final q.s. Rapidly cool to 40° C. once the emulsion is formed. Continue mixing until room temperature is reached.

LOTION BASE WITH DIPHENHYDRAMINE HYDROCHLORIDE EXAMPLE #17

| Ingredients | Approximate Percent (w/w) |
| --- | --- |
| Propylene Glycol | 2.0% |
| Diphenhydramine Hydrochloride USP | 2.0% |
| Methyl paraben NF | 0.2% |
| Propyl paraben NF | 0.1% |
| Promulgen D | 6.0% |

LOTION BASE WITH
DIPHENHYDRAMINE HYDROCHLORIDE EXAMPLE #17

| Ingredients | Approximate Percent (w/w) |
|---|---|
| Polyoxyl 40 Stearate NF | 4.0% |
| Arlacel 165 | 10.0% |
| Isopropyl Myristate | 5.0% |
| Isostearyl Alcohol | 5.0% |
| Kukui Nut Oil | 2.0% |
| Dimethicone | 1.0% |
| Fragrance (optional) | q.s. |
| Purified Water | q.s. ad 100.0% |

Heat a portion of the water to 65°–70° C. Disperse the methyl paraben in the propylene glycol and add to the water with agitation. Add the diphenhydramine and dissolve. Melt the polyoxyl 40 stearate, Promulgen D, Arlacel, , isopropyl myristate, isostearyl alcohol, and kukui nut oil together at 65°–70° C. Dissolve the propyl paraben in the oils. Then add the oil phase to the water phase with rapid mixing. Remove heat and add the dimethicone and fragrance. Perform the final q.s. Rapidly cool to 40° C. once the emulsion is formed. Continue mixing until room temperature is reached.

LOTION BASE WITH DIPHENHYDRAMINE HYDROCHLORIDE
AND ZINC OXIDE EXAMPLE #18

| Ingredients | Approximate Percent (w/w) |
|---|---|
| Propylene Glycol | 2.0% |
| Diphenhydramine Hydrochloride | 2.0% |
| Zinc Oxide | 2.0% |
| Methyl paraben NF | 0.2% |
| Propyl paraben NF | 0.1% |
| Promulgen D | 6.0% |
| Polyoxyl 40 Stearate NF | 4.0% |
| Arlacel 165 | 10.0% |
| Isopropyl Myristate | 5.0% |
| Isostearyl Alcohol | 5.0% |
| Kukui Nut Oil | 2.0% |
| Dimethicone | 1.0% |
| Fragrance (optional) | q.s. |
| Purified Water | q.s. ad 100.0% |

Heat a portion of the water to 65°–70° C. Disperse the methyl paraben in the propylene glycol and add to the water with agitation. Add the diphenhydramine and dissolve. Dispense the zinc oxide in the aqueous solution. Melt the polyoxyl 40 stearate, Promulgen D, Arlacel, isopropyl myristate, isostearyl alcohol, and kukui nut oil together at 65°–70° C. Dissolve the propyl paraben in the oils. Then add the oil phase to the water phase with rapid mixing. Remove heat and add the dimethicone and fragrance. Perform the final q.s. Rapidly cool to 40° C. once the emulsion is formed. Continue mixing until room temperature is reached.

CREAM BASE WITH UREA EXAMPLE #19

| Ingredients | Approximate Percent (w/w) |
|---|---|
| Propylene Glycol | 2.0% |
| Urea | 10.0% |
| Methyl paraben NF | 0.2% |
| Propyl paraben NF | 0.1% |
| Promulgen D | 8.0% |
| Polyoxyl 40 Stearate NF | 4.0% |
| Arlacel 165 | 10.0% |
| Isopropyl Myristate | 5.0% |
| Isostearyl Alcohol | 5.0% |
| Kukui Nut Oil | 2.0% |
| Dimethicone | 1.0% |
| Fragrance (optional) | q.s. |
| Purified Water | q.s. ad 100.0% |

Heat a portion of the water to 65°–70° C. Disperse the methyl paraben in the propylene glycol and add to the water with agitation. Add the urea and dissolve. Melt the Promulgen D, Arlacel, polyoxyl 40 stearate, isopropyl myristate, isostearyl alcohol, and kukui nut oil together at 65°–70° C. Dissolve the propyl paraben in the oils. Then add the oil phase to the water phase with rapid mixing. Remove heat and add the dimethicone and fragrance. Perform the final q.s. Rapidly cool to 40° C. once the emulsion is formed. Continue mixing until room temperature is reached.

CREAM BASE WITH SENSATE EXAMPLE #20

| Ingredients | Approximate Percent (w/w) |
|---|---|
| Propylene Glycol | 2.0% |
| Methyl paraben NF | 0.2% |
| Propyl paraben NF | 0.1% |
| Promulgen D | 8.0% |
| Polyoxyl 40 Stearate NF | 4.0% |
| Arlacel 165 | 10.0% |
| Isopropyl Myristate | 5.0% |
| Isostearyl Alcohol | 5.0% |
| Kukui Nut Oil | 2.0% |
| Dimethicone | 1.0% |
| Menthyl Lactate | 2.0% |
| Fragrance (optional) | q.s. |
| Purified Water | q.s. ad 100.0% |

Heat a portion of the water to 65°–70° C. Disperse the methyl paraben in the propylene glycol and add to the water with agitation. Melt the Promulgen D, Arlacel, polyoxyl 40 stearate, isopropyl myristate, isostearyl alcohol, and kukui nut oil together at 65°–70° C. Dissolve the propyl paraben in the oils. Then add the oil phase to the water phase with rapid mixing. Remove heat and add the dimethicone, menthyl lactate, and fragrance. Perform the final q.s. Rapidly cool to 40° C. once the emulsion is formed. Continue mixing until room temperature is reached.

CREAM BASE WITH ANALGESIC EXAMPLE #21

| Ingredients | Approximate Percent (w/w) |
|---|---|
| Propylene Glycol | 2.0% |
| Methyl paraben NF | 0.2% |
| Propyl paraben NF | 0.1% |
| Promulgen D | 8.0% |
| Polyoxyl 40 Stearate NF | 4.0% |
| Arlacel 165 | 10.0% |
| Isopropyl Myristate | 5.0% |
| Isostearyl Alcohol | 5.0% |
| Kukui Nut Oil | 2.0% |
| Dimethicone | 1.0% |
| Capsaicin Alkaloid | 0.02% |
| Fragrance (optional) | q.s. |
| Purified Water | q.s. ad 100.0% |

Heat a portion of the water to 65°–70° C. Disperse the methyl paraben in the propylene glycol and add to the water with agitation. Melt the Promulgen D, Arlacel, polyoxyl 40 stearate, isopropyl myristate, isostearyl alcohol, and kukui nut oil together at 65°–70° C. Dissolve the propyl paraben and the capsaicin in the oils. Then add the oil phase to the water phase with rapid mixing. Remove heat and add the dimethicone and fragrance. Perform the final q.s. Rapidly cool to 40° C. once the emulsion is formed. Continue mixing until room temperature is reached.

CREAM BASE WITH SENSATE EXAMPLE #22

| Ingredients | Approximate Percent (w/w) |
|---|---|
| Propylene Glycol | 2.0% |
| Methyl paraben NF | 0.2% |
| Propyl paraben NF | 0.1% |
| Promulgen D | 8.0% |
| Polyoxyl 40 Stearate NF | 4.0% |
| Arlacel 165 | 10.0% |
| Isopropyl Myristate | 5.0% |
| Isostearyl Alcohol | 5.0% |
| Kukui Nut Oil | 2.0% |
| Dimethicone | 1.0% |
| Methyl nicotinate | 0.5% |
| Fragrance (optional) | q.s. |
| Purified Water | q.s. ad 100.0% |

Heat a portion of the water to 65°–70° C. Disperse the methyl paraben in the propylene glycol and add to the water with agitation. Melt the Promulgen D, Arlacel, polyoxyl 40 stearate, isopropyl myristate, isostearyl alcohol, and kukui nut oil together at 65°–70° C. Dissolve the propyl paraben and the methyl nicotinate in the oils. Then add the oil phase to the water phase with rapid mixing. Remove heat and add the dimethicone and fragrance. Perform the final q.s. Rapidly cool to 40° C. once the emulsion is formed. Continue mixing until room temperature is reached.

CREAM BASE WITH HYDROCORTISONE & UREA EXAMPLE #23

| Ingredients | Approximate Percent (w/w) |
|---|---|
| Propylene Glycol | 2.0% |
| Hydrocortisone | 1.0% |
| Urea | 4.0% |
| Methyl paraben NF | 0.2% |
| Propyl paraben NF | 0.1% |
| Promulgen D | 8.0% |
| Polyoxyl 40 Stearate NF | 4.0% |
| Arlacel 165 | 10.0% |
| Isopropyl Myristate | 5.0% |
| Isostearyl Alcohol | 5.0% |
| Kukui Nut Oil | 2.0% |
| Dimethicone | 1.0% |
| Fragrance (optional) | q.s. |
| Purified Water | q.s. ad 100.0% |

Heat a portion of the water to 65°–70° C. Disperse the methyl paraben in the propylene glycol and add to the water with agitation. Add the urea and dissolve. Add the polyoxyl 40 stearate and dissolve. Add the hydrocortisone and disperse using a high shear mixer or similar. Melt the Promulgen D, Arlacel, isopropyl myristate, isostearyl alcohol, and kukui nut oil together at 65°–70° C. Dissolve the propyl paraben in the oils. Then add the oil phase to the water phase with rapid mixing. Remove heat and add the dimethicone and fragrance. Perform the final q.s. Rapidly cool to 40° C. once the emulsion is formed. Continue mixing until room temperature is reached.

What is claimed is:

1. A pharmaceutical composition comprising:
   a) an effective amount of dermopharmaceutical active agent,
   b) about 1.0% to about 10% of kukui nut oil by weight of the total composition, and
   c) up to about 98% by weight of the total composition of a pharmaceutically acceptable base which comprises ingredients selected from the group consisting of propylene glycol, glycerin, xanthin gum, methyl paraben, propyl paraben, stearic acid, menthyl lactate, cetearyl alcohol (and) ceteareth 20, polyoxyl 40 stearate, glyceryl stearate (and) PEG-100 stearate, isopropyl myristate, isopropyl alcohol, oleyl alcohol, oleic acid, dimethicone, or $C_{12}$–$C_{15}$ alcohols benzoate and purified water.

2. The composition according to claim 1 wherein the kukui nut oil is present at a concentration about 2% by weight of the total composition.

3. The composition according to claim 1 wherein the dermopharmaceutical active agent is a corticosteroid, antibiotic, antihistamine, antifungal, anesthetic, or analgesic.

4. A pharmaceutical composition according to claim 1 which is
   a) about 0.5% to 2.5% hydrocortisone,
   b) about 2.0% kukui nut oil, and
   c) a pharmaceutically acceptable base comprising.

| propylene glycol | about 2.0% |
|---|---|
| methyl paraben | about 0.2% |
| propyl paraben | about 0.1% |
| cetearyl alcohol (and) ceteareth 20 | about 8.0% |
| polyoxyl 40 stearate | about 4.0% |
| glyceryl stearate (and) PEG-100 stearate | about 10.0% |
| isopropyl myristate | about 5.0% |
| isostearyl alcohol | about 5.0% |
| dimethicone | about 1.0% |
| fragrance (optional) | q.s. |
| purified water | q.s. ad 100.0% |

5. A pharmaceutical composition according to claim 4 wherein the amount of hydrocortisone is 1.0% by weight of the total composition.

6. A pharmaceutical composition according to claim 1 which is
   a) about 0.5% to about 4% lidocaine hydrochloride,
   b) about 2.0% kukui nut oil, and
   c) a pharmaceutically acceptable base comprising

| propylene glycol | about 2.0% |
|---|---|
| methyl paraben | about 0.2% |
| propyl paraben | about 0.1% |
| cetearyl alcohol (and) ceteareth 20 | about 4.0–6.0% |
| polyoxyl 40 stearate | about 2.0–4.0% |
| glyceryl stearate (and) PEG-100 stearate | about 10.0% |
| isopropyl myristate | about 5.0% |
| isostearyl alcohol | about 5.0% |
| dimethicone | about 1.0–2.0% |
| fragrance (optional) | q.s. |
| purified water | q.s. ad 100.0%. |

7. A pharmaceutical composition according to claim 6 wherein the amount of lidocaine hydrochloride is 4.0% by weight of the total composition.

8. A pharmaceutical composition according to claim 1 which is
   a) about 0.5% to 2.5% diphenhydramine hydrochloride,
   b) about 2.0% kukui nut oil, and c) a pharmaceutically acceptable base comprising

| | |
|---|---|
| propylene glycol | about 2.0% |
| methyl paraben | about 0.2% |
| propyl paraben | about 0.1% |
| cetearyl alcohol (and) ceteareth 20 | about 6.0% |
| polyoxyl 40 stearate | about 4.0% |
| glyceryl stearate (and) PEG-100 stearate | about 10.0% |
| isopropyl myristate | about 5.0% |
| isostearyl alcohol | about 5.0% |
| dimethicone | about 1.0% |
| fragrance (optional) | q.s. |
| purified water | q.s. ad 100.0%. |

9. A pharmaceutical composition according to claim 8 wherein the amount of diphenhydramine hydrochloride is 2.0% by weight of the total composition.

10. A pharmaceutical composition according to claim 1 which is a) about 2.0% zinc oxide, b) about 2.0% of diphenhydramine hydrochloride, c) about 2.0% kukui nut oil, and d) a pharmaceutically acceptable base comprising

| | |
|---|---|
| propylene glycol | about 2.0% |
| methyl paraben | about 0.2% |
| propyl paraben | about 0.1% |
| cetearyl alcohol (and) ceteareth 20 | about 6.0% |
| polyoxyl 40 stearate | about 4.0% |
| glyceryl stearate (and) PEG-100 stearate | about 10.0% |
| isopropyl myristate | about 5.0% |
| isostearyl alcohol | about 5.0% |
| dimethicone | about 1.0% |
| fragrance (optional) | q.s. |
| purified water | q.s. ad 100.0%. |

11. A pharmaceutical composition according to claim 1 which is a) about 10% urea, b) about 2.0% kukui nut oil, and c) a pharmaceutically acceptable base comprising

| | |
|---|---|
| propylene glycol | about 2.0% |
| methyl paraben | about 0.2% |
| propyl paraben | about 0.1% |
| cetearyl alcohol (and) ceteareth 20 | about 8.0% |
| polyoxyl 40 stearate | about 4.0% |
| glyceryl stearate (and) PEG-100 stearate | about 10.0% |
| isopropyl myristate | about 5.0% |
| isostearyl alcohol | about 5.0% |
| dimethicone | about 1.0% |
| fragrance (optional) | q.s. |
| purified water | q.s. ad 100.0%. |

12. A pharmaceutical composition according to claim 1 which is a) about 0.02% capsaicin alkaloid, b) about 2.0% kukui nut oil, and c) a pharmaceutically acceptable base comprising

| | |
|---|---|
| propylene glycol | about 2.0% |
| methyl paraben | about 0.2% |
| propyl paraben | about 0.1% |
| cetearyl alcohol (and) ceteareth 20 | about 8.0% |
| polyoxyl 40 stearate | about 4.0% |
| glyceryl stearate (and) PEG-100 stearate | about 10.0% |
| isopropyl myristate | about 5.0% |
| isostearyl alcohol | about 5.0% |
| dimethicone | about 1.0% |
| fragrance (optional) | q.s. |
| purified water | q.s. ad 100.0%. |

13. A pharmaceutical composition according to claim 1 which is a) about 1.0% of hydrocortisone, b) about 4.0% of urea, c) about 2.0% kukui nut oil, and d) a pharmaceutically acceptable base comprising

| | |
|---|---|
| propylene glycol | about 2.0% |
| methyl paraben | about 0.2% |
| propyl paraben | about 0.1% |
| cetearyl alcohol (and) ceteareth 20 | about 8.0% |
| polyoxyl 40 stearate | about 4.0% |
| glyceryl stearate (and) PEG-100 stearate | about 10.0% |
| isopropyl myristate | about 5.0% |
| isostearyl alcohol | about 5.0% |
| dimethicone | about 1.0% |
| fragrance (optional) | q.s. |
| purified water | q.s. ad 100.0%. |

\* \* \* \* \*